(12) United States Patent
Krishnan

(10) Patent No.: US 7,824,341 B2
(45) Date of Patent: Nov. 2, 2010

(54) METHOD AND APPARATUS FOR LOCATING THE FOSSA OVALIS AND PERFORMING TRANSSEPTAL PUNCTURE

(75) Inventor: Subramaniam C. Krishnan, West Bloomfield, MI (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 402 days.

(21) Appl. No.: 11/901,755

(22) Filed: Sep. 19, 2007

(65) Prior Publication Data

US 2008/0103400 A1 May 1, 2008

Related U.S. Application Data

(62) Division of application No. 10/648,844, filed on Aug. 25, 2003.

(60) Provisional application No. 60/405,849, filed on Aug. 24, 2002.

(51) Int. Cl.
*A61B 5/05* (2006.01)

(52) U.S. Cl. .................. 600/508; 600/374; 600/424; 607/1; 607/70; 607/74; 607/115; 607/116; 607/118

(58) Field of Classification Search .................. None
See application file for complete search history.

(56) References Cited

U.S. PATENT DOCUMENTS

| 4,562,846 | A | * | 1/1986 | Cox et al. | .................. 600/509 |
|---|---|---|---|---|---|
| 5,336,252 | A | | 8/1994 | Cohen | |
| 5,409,008 | A | | 4/1995 | Svenson et al. | |
| 5,494,042 | A | | 2/1996 | Panescu et al. | |
| 5,497,774 | A | | 3/1996 | Swartz et al. | |
| 5,617,854 | A | | 4/1997 | Munsif | |
| 5,983,126 | A | | 11/1999 | Wittkampf | |
| 6,001,085 | A | | 12/1999 | Lurie et al. | |
| 6,047,218 | A | | 4/2000 | Whayne et al. | |

(Continued)

FOREIGN PATENT DOCUMENTS

WO 0178596 10/2001

(Continued)

OTHER PUBLICATIONS

Bidoggia et al, "Transseptal Left Heart Catheterization: Usefulness of the Intracavitary Electrocardiogram in the Localization of the Fossa Ovalis" Catheterization and Cardiovascular Diagnosis, 24, 1991, pp. 221-225.

(Continued)

*Primary Examiner*—Carl H Layno
*Assistant Examiner*—Deborah Malamud
(74) *Attorney, Agent, or Firm*—Wiley Rein LLP

(57) ABSTRACT

A method of identifying the fossa ovalis in a patient by positioning one or more electrodes against the tissue of the interatrial septum of the patient and acquiring unipolar and/or bipolar electrograms of the tissue of the interatrial septum while moving the electrodes to a plurality of positions against the tissue of the interatrial septum. The fossa ovalis is identified on the basis of unipolar voltage reduction, signal fractionation, broadened signal, reduced signal slew rate, reduced local myocardial impedance, increased phase angle and/or increased pacing threshold. An apparatus for identify the fossa ovalis is also provided.

19 Claims, 6 Drawing Sheets

U.S. PATENT DOCUMENTS

| | | | |
|---|---|---|---|
| 6,328,699 | B1 | 12/2001 | Eigler et al. |
| 6,606,513 | B2 | 8/2003 | Lardo et al. |
| 6,623,474 | B1 | 9/2003 | Ponzi |
| 7,047,068 | B2 * | 5/2006 | Haissaguerre .............. 600/547 |
| 2002/0161422 | A1 | 10/2002 | Swanson et al. |
| 2002/0169377 | A1 | 11/2002 | Khairkhahan et al. |
| 2003/0144657 | A1 | 7/2003 | Bowe et al. |
| 2003/0208141 | A1 | 11/2003 | Worley et al. |
| 2004/0133113 | A1 | 7/2004 | Krishnan |
| 2004/0220497 | A1 | 11/2004 | Findlay et al. |

FOREIGN PATENT DOCUMENTS

| WO | 02058780 | 8/2002 |
|---|---|---|

OTHER PUBLICATIONS

Supplementary European Search Report dated Apr. 4, 2008 pertaining to corresponding EPO application No. 03797867.3.

Ran Kornowski, et al., "Electromagnetic Guidance for Catheter-Based Transendocardial Injection: A Platform for Intramycocardial Angiogenesis Therapy", Journal of American College of Cardiology, vol. 35, No. 4, 2000.

Eugene Braunwald, "Transseptal Left Heart Catheterization", Supplement III to Circulation, vol. XXXVII and XXXVIII, May 1968.

Lior Gepstein, et al., "A Novel Method for Nonfluoroscopic Catheter-Based Electroanatomical Mapping of the Heart", American Heart Association, 1997.

Frank X. Roithinger, et al., "Use of Electroanatomic Mapping to Delineate Transseptal Atrial Conduction in Humans", American Heart Association, 1999.

Douglas Beinborn, et al., "'GPS' for the Heart", EP Lab Digest.

Frank X. Roithinger, et al., "Clinical Assessment of Atrial Activation—Current Methods and Future Perspectives".

Mario D. Gonzalez, et al., "Transseptal Left Heart Catheterization for Cardiac Ablation Procedures", Journal of Interventional Cardiac Electrophysiology, 2001, pp. 89-95.

Roithinger, et al., Use of Electroanatomic Mapping to Delineate Transseptal Atrial Conduction in Humans, American Heart Association, Circulation 1999;100; pp. 1791-1797.

Wittkampf, et al., LocaLisa: New Technique for Real-Time 3-Dimensional Localization of Regular Intracardiac Electrodes, American Heart Association, Circulation 1999;99; pp. 1312-1317.

* cited by examiner

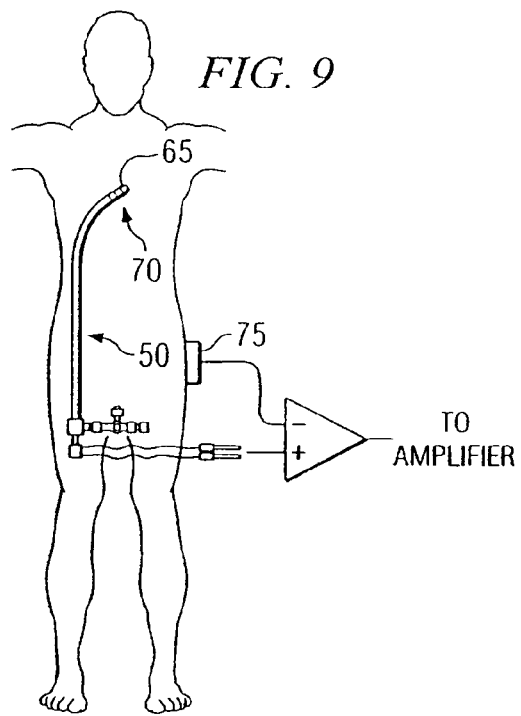
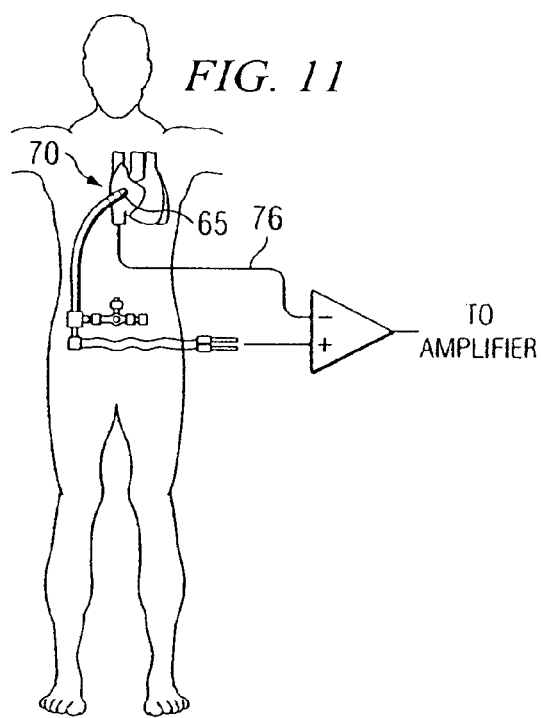
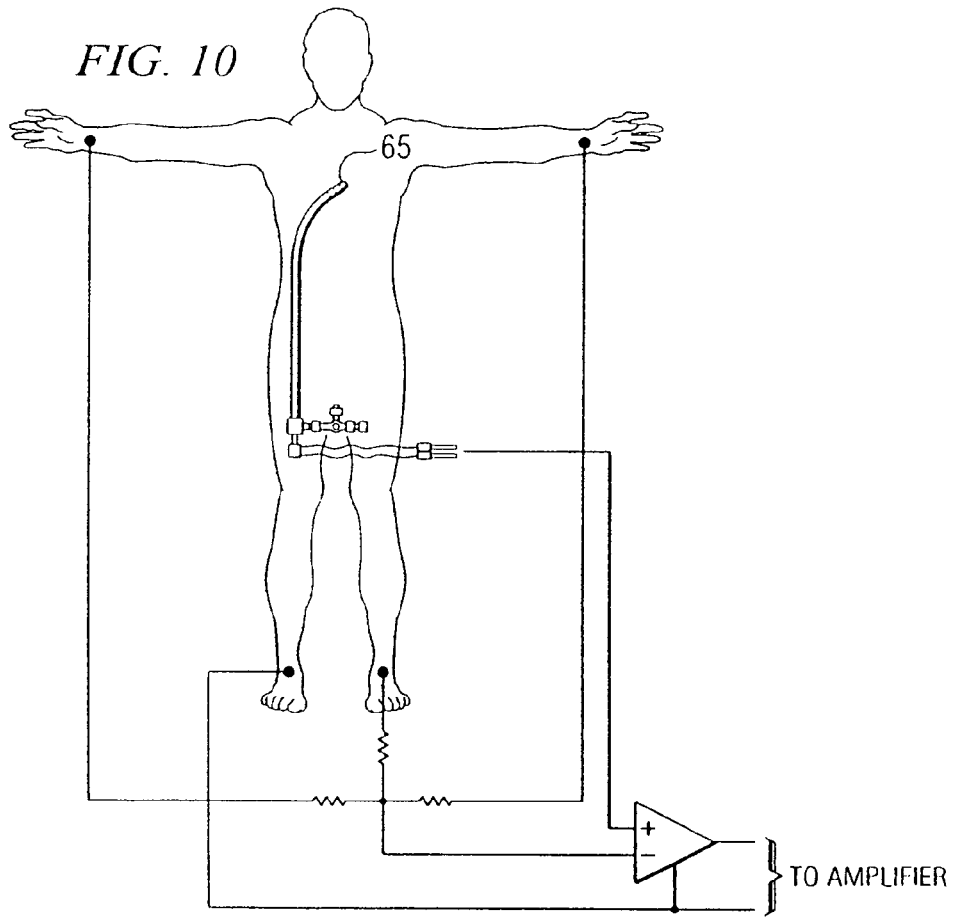

ness needed. Additional techniques which may be used to locate the fossa ovalis include biplane fluoroscopy, pressure manometry, contrast infusion as well as surface, transesophageal or intracardiac echocardiography (i.e., ultrasound).

While echocardiography can be useful, there are potential problems in using these techniques to locate the fossa ovalis. Contact of the transseptal dilator and the tenting of the membrane of the fossa ovalis that one looks for with echo guidance may be missed depending on the area of the fossa that is cut by the ultrasound beam. If a different portion of the membrane is tented by the dilator tip, this may not be apparent in the ultrasound picture. If transesophageal echocardiography (TEE) is used to guide the puncture, a different operator has to operate the TEE system and therefore errors can occur especially in the interpretation of the data. For example a different catheter (other than the transseptal dilator) may be tenting the fossa. Cardiac tamponade and other complications are known to have occurred during transseptal punctures performed in electrophysiology laboratories despite the routine use of ultrasound guidance. The placement and use of ultrasound catheters also often require the insertion of large intravascular sheaths. The additional time and expense that the use of ultrasound catheters and sheaths incurs is not inconsiderable and this can make it impractical to use them routinely.

METHOD AND APPARATUS FOR LOCATING THE FOSSA OVALIS AND PERFORMING TRANSSEPTAL PUNCTURE

CROSS-REFERENCE TO RELATED APPLICATION

The present application is a divisional application of U.S. patent application Ser. No. 10/648,844, filed on Aug. 25, 2003, which claims the benefit of U.S. Provisional Patent Application Ser. No. 60/405,849, filed on Aug. 24, 2002, the entire disclosures of which are hereby incorporated herein by reference.

BACKGROUND OF THE INVENTION

1. Field of the Invention

The present invention relates to methods and apparatus for locating the fossa ovalis, as well as methods and apparatus for performing transseptal punctures.

2. Description of Related Art

The transseptal puncture for left atrial and left ventricular catheterization was initially described simultaneously by Ross and Cope in 1959. In the 1960s, Brockenbrough and colleagues modified the design of the transseptal needle and the guiding catheter. In the late 1960s and 70s, its use declined because of the occurrence of complications and because of the development of selective coronary arteriography which led to the refinement of catheterization of the left side of the heart by the retrograde approach. With the advent of percutaneous balloon mitral valvuloplasty, antegrade percutaneous aortic valvuloplasty as well as catheter ablation of arrhythmias arising from the left atrium (or utilizing left sided bypass tracts), the transseptal puncture technique for access to the left atrium and ventricle has made a strong comeback.

The goal of transseptal catheterization is to cross from the right atrium to the left atrium through the fossa ovalis. Mechanical puncture of this area with a needle and catheter combination is required for the procedure. Typically, a guidewire is inserted through the right femoral vein and advanced to the superior vena cava. A sheath (typically about 66 cm long) is placed over a dilator (typically about 70 cm long) that is advanced over the guidewire into the superior vena cava. The guidewire is then removed and a 71 cm Brockenbrough needle is advanced up to the dilator tip. The apparatus is dragged down into the right atrium, along the septum. When the dilator tip is positioned adjacent the fossa ovalis (some times determined under ultrasound guidance), the needle is then pushed forward so that it extends past the dilator tip, through the fossa ovalis into the left atrium. The dilator and sheath may then be pushed through the fossa ovalis over the needle. The dilator and needle are then removed, leaving the sheath in place in the left atrium. Thereafter, catheters may be inserted through the sleeve into the left atrium in order to perform various necessary procedures.

The danger of the transseptal approach lies in the possibility that the needle and catheter will puncture an adjacent structure such as the aorta, the coronary sinus or the free wall of the atrium. In the Cooperative study on Cardiac Catheterization, a 0.2% mortality rate, 6% incidence rate of major complications and 3.4% incidence of serious complications were reported including 43 perforations. To minimize this risk, the operator must have a detailed familiarity with the regional anatomy of the atrial septum. Due to the potentially life threatening complications of the procedure, many operators feel that fluoroscopy, which at best represents an epicardial shadow of the heart, is not enough and additional tools are

SUMMARY OF THE INVENTION

The present invention provides a method of identifying the fossa ovalis in a patient, comprising the steps of:
(a) positioning one or more electrodes against the tissue of the interatrial septum of the patient;
(b) acquiring unipolar and/or bipolar electrograms of the tissue of the interatrial septum, while moving the electrodes to a plurality of positions against the tissue of the interatrial septum; and
(c) identifying the fossa ovalis on the basis of at least one of the following parameters:
unipolar voltage reduction
signal fractionation
broadened signal
reduced signal slew rate
reduced local myocardial impedance
increased phase angle and
increased pacing threshold.

The fossa ovalis may also be identified on the basis of bipolar voltage reduction. In addition, the fossa ovalis may be identified on the basis of at least two of the parameters noted above.

The present invention also provides a method of performing a transseptal puncture on a patient, comprising the steps of:
(a) positioning one or more electrodes against the tissue of the interatrial septum of the patient;
(b) acquiring unipolar and/or bipolar electrograms of the tissue of the interatrial septum, while moving the electrodes to a plurality of positions against the tissue of the interatrial septum;
(c) identifying the fossa ovalis on the basis of at least one of the following parameters:
unipolar voltage reduction
signal fractionation
broadened signal
reduced signal slew rate
reduced local myocardial impedance
increased phase angle and
increased pacing threshold
and (d) penetrating the interatrial septum through the fossa ovalis in order to access the left atrium.

In the above method, the one or more electrodes may be provided on the distal end of a catheter and the positioning step may comprise positioning the distal end of the catheter against the tissue of the interatrial septum of the patient. In addition, the penetrating step may comprise urging a needle through the interior of the catheter and through the fossa ovalis into the left atrium. This method may also include the step of observing ST segment elevation in the unipolar electrogram in order to ensure that the distal end of the catheter is in contact with the tissue of the interatrial septum.

The present invention also provides a catheter for use in transseptal punctures, comprising:

(a) a hollow lumen having a distal end;
(b) a first electrode positioned at the distal end; and
(c) a second electrode positioned on the catheter and spaced proximally from the first electrode.

BRIEF DESCRIPTION OF THE DRAWINGS

FIG. 9 is a schematic illustration of the use of the transseptal apparatus of FIG. 7 for obtaining unipolar electrograms, using a skin patch as the indifferent (or reference) electrode;

FIG. 10 is a schematic illustration of the use of the transseptal apparatus of FIG. 7 for obtaining unipolar electrograms, using a Wilson's central terminal as the indifferent electrode; and FIG. 11 is a schematic illustration of the use of the transseptal apparatus of FIG. 7 for obtaining unipolar electrograms, using separate conventional EP catheter place in the inferior vena cava as the indifferent electrode.

DETAILED DESCRIPTION

Figure 1A:
FIG. 1 is a light microscopy tissue section from a human atrial septum.
Figure 1B:
Figure 1C:
Figure 1D:
Figure 1E:
Figure 1F:

Applicant has discovered that the fossa ovalis can be located by measuring electrophysiological activity of the tissue of the interatrial septum. In addition, Applicant has also developed an apparatus which may be used not only for locating the fossa ovalis, but also for performing transseptal punctures through the fossa ovalis.

The fossa ovalis is the depression at the site of the fetal interatrial communication termed the foramen ovale. In fetal life, this communication allows richly oxygenated IVC blood coming from the placenta to reach the left atrium and has a well-marked rim or limbus superiorly. The floor of the fossa ovalis is a thin, fibromuscular partition. In fact, because the fossa ovalis is thinner than the rest of the interatrial septum, light may even be used to selectively transilluminate the fossa ovalis.

However, in addition to being thinner than the surrounding tissue of the interatrial septum, Applicant has discovered that the fossa ovalis has considerable scar tissue. Autopsy studies done on human hearts (with Masson trichrome stain and microscopy/morphometric analysis with NIH image program) revealed that the fossa ovalis has significantly more fibrous tissue that the non fossa portion of the interatrial septum. Specifically, the non fossa portion of the interatrial septum consistently had around 70% muscle and 30% fibrous tissue, whereas the fossa ovalis had an average of 33% muscle and 67% fibrous tissue.

FIG. 1 is a light microscopy tissue section from a human atrial septum with hematoxylin & eosin staining (panels A, C & E) as well as Masson trichrome stain (panels B, D & F). Panels A & B show the superior limbus as well as the membrane of the fossa ovalis. Panels C & D show the superior limbus of the interatrial septum, while panels E & F show the membrane of the fossa ovalis. As noted from FIG. 1, the fossa ovalis has significantly more fibrous scar tissue than other portions of the interatrial septum. Applicant has found that this increased scar tissue, coupled with the reduced thickness of the fossa ovalis, allows one to locate the fossa by measuring electrophysiological activity of the region.

In particular, Applicant has found that the fossa ovalis may be located by measuring the electrophysiological ("EP") activity of the fossa ovalis and surrounding heart tissue. By observing differences in the EP activity of tissue at various locations, the operator may determine the location of the fossa ovalis. The lower muscle content and higher fibrous tissue content of the fossa ovalis with respect to the rest of the interatrial septum, as well as the relative "thinning" of the fossa, results in changes in EP activity which may be readily observed via an intracardiac electrogram. For example, the fossa ovalis will record broader, fractionated electrograms of lower amplitude and lower slew rates. Based upon these surprising findings, one or more electrodes for acquiring EP data may be incorporated into a catheter/dilator used during transseptal puncture.

Intracardiac electrograms are typically performed by positioning a probe having one or more electrodes against the cardiac tissue to be examined. The probe is typically inserted into the heart through a vein or artery via a sheath. A recording device (well-known to those skilled in the art) is used to record and display an electrical signal produced by the cardiac tissue. When a unipolar probe is used, the lead from the single electrode on the probe is connected to the positive terminal of a recording device or amplifier, and an indifferent (or reference) electrode is then connected to the negative terminal of the recording device or amplifier. The indifferent electrode is simply another electrode which is located away from the "exploring" electrode—typically positioned within or against a structure in which no electrical activity takes place. The reference electrode may comprise a skin patch, a plurality of electrodes placed at various locations on the patient's body (i.e., Wilson's central terminal), or even an electrode placed in a separate catheter positioned in a large vein (e.g., the inferior vena cava). For unipolar electrograms, the electrogram will display the difference in electrical potential between the unipolar electrode positioned against the cardiac tissue and the electrode connected to the negative electrode.

For bipolar electrograms, the probe typically comprises two electrodes spaced apart from one another by a short distance (typically less than about 5 mm) in a single probe. The leads from the two electrodes are connected to a junction box of a recording device.

A signal in an intracardiac electrogram is characterized in terms of its amplitude (typically measured in millivolts), its duration (measured in milliseconds) and its slew rate (measured in volts per second). The amplitude of an electrogram depends on several factors, including the mass of myocardium underlying the electrode, the contact of the electrode with the myocardium, the orientation of the electrode with respect to the axis of depolarization, and the presence of any inexcitable tissue (i.e., fibrous or connective tissue) between the myocytes and the electrode. Electrodes that are in contact with infarcted ventricular myocardium or those that have become encapsulated with a thick layer of fibrous tissue, for example, typically show a lower amplitude electrogram than those directly in contact with healthy myocytes. The slew rate represents the maximal rate of change of the electrical signal between the sensing electrodes and, mathematically, is the first derivative of the electrogram (dv/dt) and is a measure of the change in electrogram voltage over time. It is generally directly related to the electrogram amplitude and duration. In the region of the fossa ovalis, the slew rate will be lower in the region of the fossa ovalis, thus following the changes in electrogram amplitude.

Figure 2:
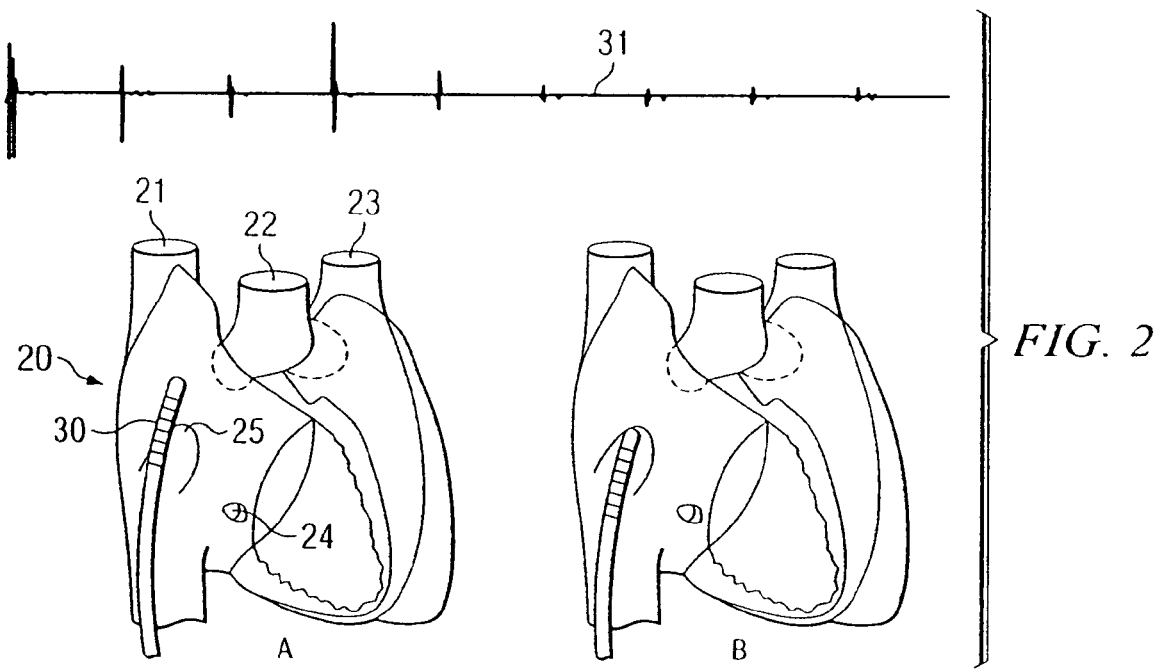
FIG. 2 is depicts the use of a quadripolar EP catheter to obtain bipolar electrograms and identify the fossa ovalis on the basis of a decrease in amplitude as the catheter is dragged inferiorly along the interatrial septum and makes contact with the fossa ovalis.

FIG. 2 depicts a bipolar electrogram acquired using a standard EP deflectable catheter 30. In FIG. 2, quadripolar EP catheter 30 is located within the right atrium, against the interatrial septum above the fossa ovalis 25 (see FIG. 2A). For point of reference, the superior vena cava is depicted at 21, the aorta at 22, the pulmonary artery at 23 and the coronary sinus at 24. As the catheter 30 is dragged inferiorly along the interatrial septum and makes contact with the fossa ovalis 25 (FIG. 2B), the bipolar electroanatomical voltage 31 drops abruptly. In fact, the region of the fossa ovalis consistently displays unipolar and bipolar electrograms of amplitudes less than about 1 mV while the rest of the interatrial septum displays electrograms greater than about 2 mV (see FIG. 3).

Figure 3:
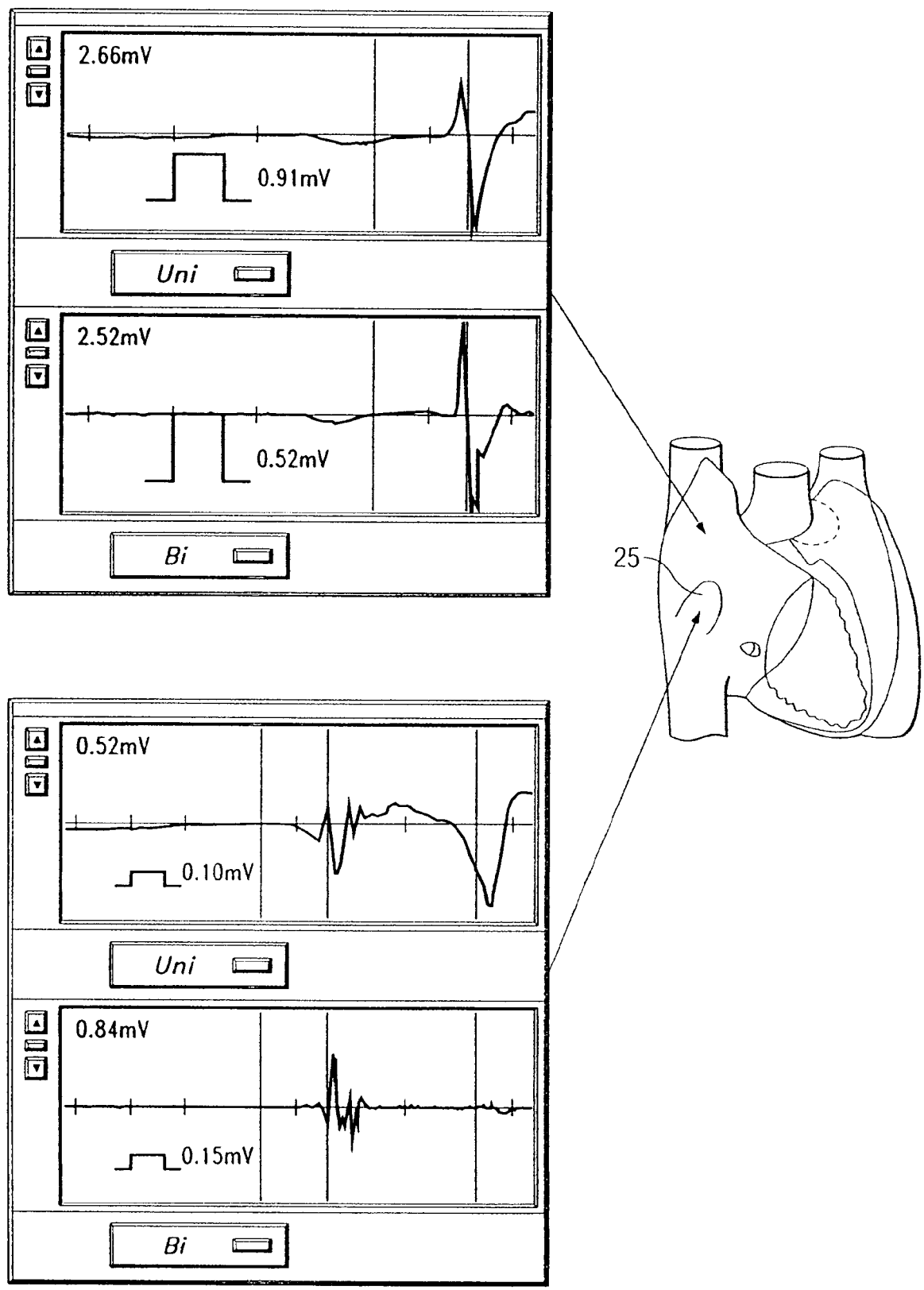
FIG. 3 depicts unipolar and bipolar electrograms taken from tissue of the interatrial septum adjacent the fossa ovalis and the fossa itself, with the fossa providing low voltage, broad and fractionated signals with low slew rates.
Figure 5A:
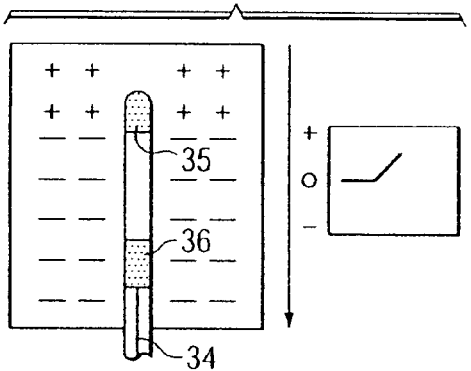
FIG. 5 is a schematic illustration of the significance of the positioning of the interelectrode axis in bipolar electrograms with respect to the orientation of the wavefront of electrical excitation.
Figure 5C:
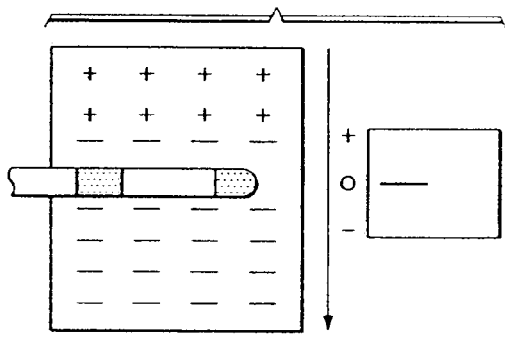
Figure 5B:
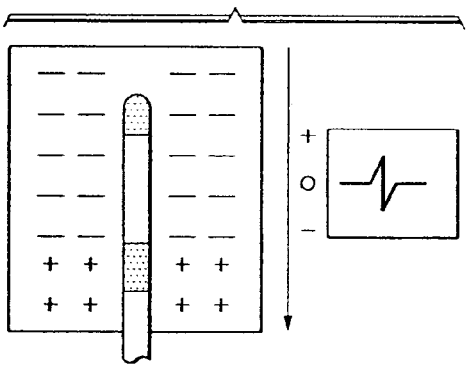
Figure 5D:
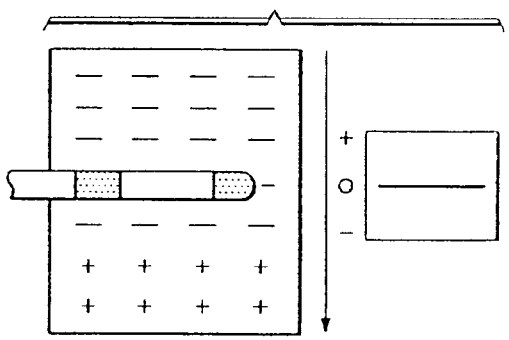

High density mapping of the interatrial septum (performed with the CARTO system available from Biosense Webster, Diamond Bar, Calif.) further revealed that the area of the fossa ovalis (posterior to the coronary sinus ostium and inferior to the His bundle) consistently shows low voltage and fractionated unipolar and bipolar electrograms. FIG. 3 depicts bipolar and unipolar electrograms obtained using the CARTO system. Panel A of FIG. 3 depicts bipolar and unipolar electrograms for a location on the interatrial septum superior to the fossa ovalis. As noted in panel A of FIG. 3, the unipolar voltage is 2.66 mV and the bipolar voltage is 2.52 mV. Panel B of FIG. 3 depicts bipolar and unipolar electrograms for the fossa ovalis 25. As noted in panel B of FIG. 3, the unipolar voltage for the fossa ovalis is 0.52 mV and the bipolar voltage is 0.84 mV. Thus, the drop in voltage for the fossa ovalis as compared to the surrounding tissue of the interatrial septum may be effectively used to locate the fossa ovalis.

As seen in FIG. 3, the region of the fossa ovalis also displays electrograms that are broad (greater than about 50 ms in duration) while the rest of the interatrial septum has signals that are less than about 35 ms in width. Bipolar electrograms also show multiple spikes or deflections (fractionation), and the unipolar electrogram is broad with a low slew rate. This fractionation in the electrogram morphology is thought to be due to the substantially greater amounts of collagen in this tissue compared to the rest of the atrium resulting in complex anisotropic conduction. With respect to the slew rate in unipolar electrograms, the slew rate observed for the fossa ovalis is less than or equal to about 0.3 volts/second, whereas the rest of the interatrial septum provides slew rates of greater than about 0.5 volts/second. Thus, the increased fractionation, increased signal width and decreased slew rate provide additional indicia of the location of the fossa ovalis.

Not only can the fossa ovalis be identified by observing reduced signal amplitude, and increased width, fractionation and slew rate, the fossa will also be evidenced by reduced local myocardial impedance and higher phase angle. Myocardial tissue impedance is considered to be a passive electrical property of both healthy and diseased tissues. The myocardial impedance (Z) is defined as the voltage (V) divided by the sinusoidal current (I) applied through it. It has been noted by several investigators that ventricular aneurysms from chronic myocardial infarctions display a lower local myocardial impedance measurement and a higher phase angle. Changes in impedance measurements were found to be reliable in identifying scar tissue and in defining the presence, extent and location of chronic myocardial infarction. The lower endocardial impedance values in scar tissues is thought to be due to an increase in the extracellular-to-intracellular volume ratio and a resultant increase in the extracellular pathways of impulse conduction. Another hypothesis is that the improved conductance may be due to the thinning of the left ventricular wall and loss of cardiac tissue mass.

Applicant has found that the lower muscle content and higher fibrous tissue content of the fossa with respect to the rest of the interatrial septum as well as the relative "thinning" of the fossa ovalis will result in the recording of lower local impedance values and thus can be used to identify the fossa ovalis. When the catheter is positioned in the superior vena cava, the system generally recorded impedance values of greater than about 130 ohms. Once the catheter descended into the right atrium, the impedance decreased to about 120 ohms or less. Dragging the catheter to the region of the fossa ovalis lowered the impedance value by about another 15 ohms. Therefore, by observing the myocardial impedance as the tip of the catheter or other probe is dragged inferiorly across the interatrial septum, the fossa ovalis also can be identified by a sharp drop in impedance (typically about 15 ohms). Similarly, the fossa ovalis can also be identified by an increase in phase angle as compared to the surrounding tissue.

Impedance may be measured, for example, using the technique described by Wolf et al, Am. J. Physiol. 2001; 280: H179-H188. A generator (such as a Stockert generator, available from Biosense Webster, Diamond Bar, Calif.) with a stabilized output amplitude, and producing a sine wave signal of 1-2 uA with a frequency of 50 kHz, is used. The output current source buffer with a high output impedance is connected to an intracardiac electrode and provided constant alternating current through the myocardial tissues. A return electrode is connected to the reference point in the circuit and placed against the patient's back. The intracardiac electrode is connected to one input of a differential amplifier and the return electrode is connected to the second input. The output of the amplifier is then passed through a band pass filter with a central frequency equal to the measuring frequency. A synchronous detector converts the AC voltage to the direct current.

The presence of greater amounts of fibrous tissue in the fossa ovalis will also result in a higher pacing threshold and thus, will serve as an additional electrophysiological measurement in identifying the fossa ovalis. "Pacing threshold" refers to the amount of current from a pacemaker electrical impulse required to capture the heart. It is heavily dependent on the amount of muscle and scar/fibrous tissue that the pacing catheter is in contact with. The more scar/fibrous tissue that is present, the higher the pacing threshold.

Thus, an electrical pacing impulse may be applied to the interatrial septum through an electrode (e.g., a standard EP deflectable catheter or even an electrode on the transseptal apparatus of the present invention described further herein). The minimum amplitude required to capture the heart is applied and the probe or catheter carrying the electrode is dragged inferiorly across the interatrial septum. As the electrode reached the fossa ovalis, the electrical impulse will no longer be of sufficient amplitude to capture the heart. For example, an electrical impulse having a pulse width duration of about 0.5 msec and an amplitude of between about 0.8 and about 1.0 V will generally be sufficient to capture the hear when applied to the interatrial septum adjacent the fossa ovalis. However, this amplitude will not be sufficient to capture the heart when applied to the fossa ovalis. Here, an amplitude of between about 1.5 and about 1.6 V is required, at a pulse width duration of 0.5 msec. Thus, the increased pacing threshold may also be used to locate the fossa ovalis.

Figure 4:
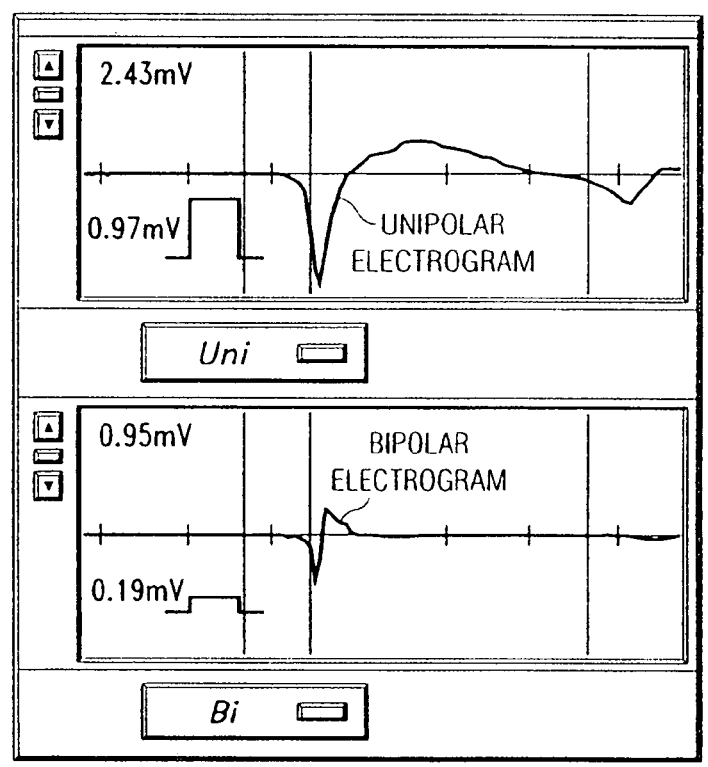
FIG. 4 depicts unipolar and bipolar electrograms taken from tissue of the interatrial septum adjacent the fossa ovalis, wherein the unipolar electrogram exhibits ST segment elevation while the bipolar electrogram does not, and the bipolar electrogram exhibits a low voltage even though the probe was not at the fossa ovalis.

In addition the various parameters described above for locating the fossa ovalis, the ST segment elevation observed in unipolar electrograms can also be advantageously employed during transseptal puncture. The unipolar electrogram of the tissue of the interatrial septum will display ST segment elevation whenever the electrode makes good tissue contact with, and exerts significant pressure against the atrial myocardium. As seen in FIG. 4, ST segment elevation is recorded in the unipolar electrogram of the interatrial septum but not the bipolar electrogram. By observing ST segment elevation, the operator can be confident that the catheter is exerting significant pressure on the myocardium for transseptal puncture (via a needle passed through the catheter).

The above mentioned electrophysiological parameters can be used to guide the transseptal puncture procedure. For example, a single electrode may be incorporated into the tip of the dilator of the transseptal apparatus (to record unipolar electrograms and other electrophysiological parameters). Alternatively, a pair of electrodes may be incorporated into the dilator in order to measure bipolar electrograms. Because there are several electrophysiological distinctions between the fossa ovalis and the rest of the atrial myocardium, the use of multiple electrophysiological parameters will add to the predictive value of the measurements made by the apparatus.

Although bipolar electrograms can be useful in locating the fossa ovalis, bipolar electrograms have a serious flaw in that if the wavefront of electrical activity travels in a direction perpendicular to the interelectrode axis, no electrical activity may be recorded. Given the potential for life threatening complications if a transseptal puncture were to be made in the wrong area of the atrium, this can literally be a fatal flaw if one were to rely solely on voltage measurements taken from bipolar electrograms. The electrophysiological basis for this flaw and other advantages of unipolar electrograms are discussed below.

Potentials generated by current sources in a volume conductor such as the heart are always recorded with respect to the potential at a reference site. Thus, it is the difference in electrical potential between the two electrodes produced by electrical currents within the myocardium that generates the intracardiac electrogram. In practice, the signal at the recording site is fed into the positive input and the reference signal into the negative input of a recording device.

A bipolar electrogram can be considered to be the instantaneous difference in potential between two unipolar electrograms recorded from two unipolar electrodes and a common remote indifferent electrode. In mathematical terms, the bipolar electrogram is equal to the unipolar electrogram from first electrode 35 minus the unipolar electrogram from second electrode 36. In other words:

BiEGM=UniEGM1−UniEGM2.

If the unipolar tip and ring electrograms have similar amplitude and timing, the two signals will cancel each other out and the resulting bipolar electrogram will be nonexistent or much smaller than either unipolar electrogram alone.

Because of this, bipolar electrograms are susceptible to the orientation of the interelectrode axis with respect to the depolarizing wavefront. As shown in panels A and B of FIG. 5, if the axis of the elongate probe (i.e., the interelectrode axis) is parallel to the direction in which the depolarizing wavefront is advancing, a sharp electrogram will be inscribed. However, if the interelectrode axis is perpendicular to the wavefront (panels C and D of FIG. 5), as the wavefront passes underneath them, the shift in potential beneath the two electrodes will be identical. The electrodes in this scenario, will record no difference in electrical potential with respect to each other. Consequently, no intracardiac electrogram is generated. In general, it is recognized that bipolar electrograms are a function of three variables: the voltage of the tip or distal electrode, the voltage of the ring or proximal electrode, and the presence of activation time difference (phase shift) between the poles or electrode. This is in contrast with unipolar electrograms where the only variable is the voltage of the tip electrode. Due to the increased number of variables, the greater variance in bipolar electrograms is not surprising. The large signal variation associated with normal respiration often seen with bipolar electrograms is additional evidence for their inconsistency.

Figure 6:
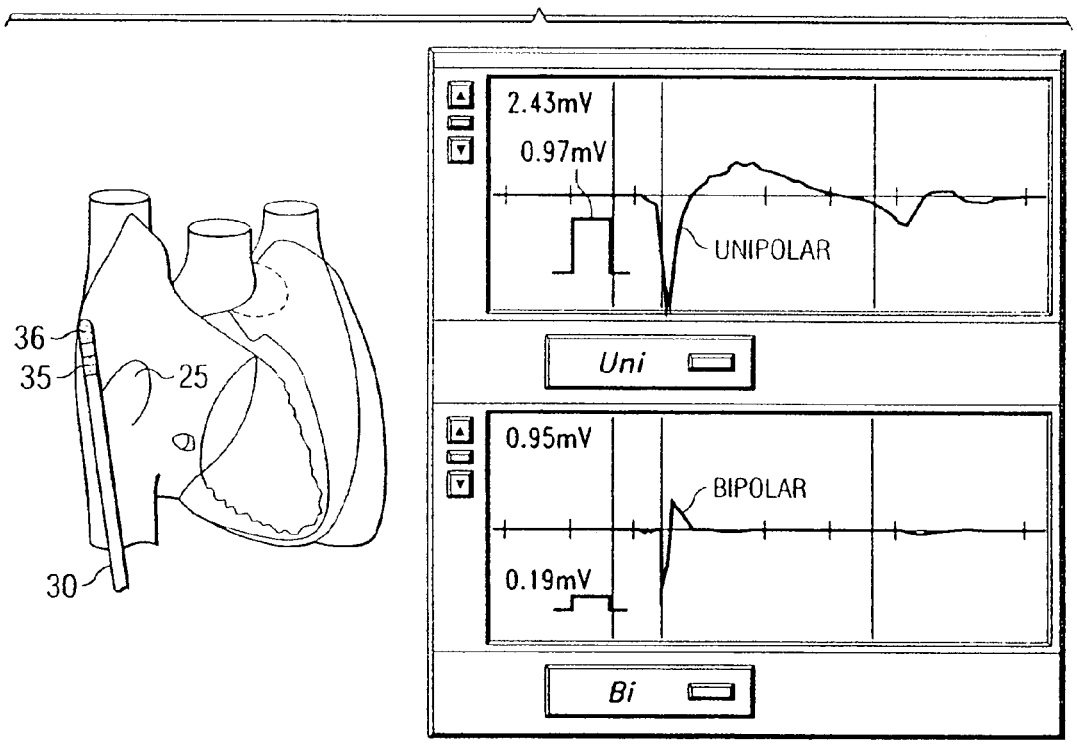
FIG. 6 is similar to FIG. 4, however the location of the probe is shown to indicate that the bipolar electrogram exhibits reduced voltage even though the probe is not at the fossa ovalis.

A dramatic illustration of the potential problems associated with relying on bipolar electrograms alone is shown in FIG. 6 which depicts a false reading of low voltage by bipolar electrogram. Here, a catheter 34 having first and second electrodes 35 and 36 is positioned such that the catheter tip (and hence both electrodes) are positioned in the posterior wall of a human atrium away from the fossa ovalis. A transseptal puncture performed at this site can have life threatening complications. However, the bipolar electrogram from this site indicates a voltage of only 0.95 mV, while the unipolar electrogram exhibits a voltage of 2.43 mV (indicating that the tip of the catheter is not at the fossa ovalis). This discrepancy is more than likely the result of unipolar EGMs recorded by the distal and proximal electrodes of the catheter being of similar amplitude and that there is no significant phase shift in timing of activation. Thus, the voltage of the bipolar electrogram signal should not be relied upon, by itself, to locate the fossa ovalis.

The principles and sensing configuration described above, i.e. recording of electrical signals from a pair of electrodes both of which are in contact with the myocardium, describe the bipolar system. In the bipolar recording mode, the reference electrode is positioned close to the exploring electrode. In the unipolar mode, the reference electrode (usually the anode) is located at an infinite distance from the recording site (cathode). Theoretically, the reference electrode is located beyond the zone of current flow that generates the electrical field at the exploring electrode. Therefore, a unipolar recording may reflect influences from both local and distant electrical events. Unipolar electrograms recorded from the heart may include activity from other parts of the heart, although their contribution decreases with distance. Simultaneous recordings of intra- and extracellular electrograms have shown that for the downstroke of the unipolar electrogram, the intrinsic deflection coincides with the upstroke of the action potential beneath the exploring electrode.

In clinical practice, during the recording of unipolar electrograms with pacemakers, the pulse generator functions as the reference electrode. In the electrophysiology laboratory, the reference electrode is usually one of the following:

a) Skin patch: A wire is connected to the skin patch and leads to the negative terminal of the amplifier. During implantation of unipolar pacemaker leads, the lead is often tested with an alligator clip connected to muscle in the exposed pocket and the other end connected to the negative terminal of the amplifier (using the same principle as the skin patch).

b) Wilson's central terminal: Central terminal created by connecting all three limb electrodes through a 5000 ohm resistor. This terminal is used as the negative pole.

c) Indifferent electrode in one of the great veins such as the inferior vena cava: A separate catheter that is connected to the negative input of the amplifier may also be placed in one of the great veins.

Investigators have found that the peak to peak amplitude of the unipolar signal correlated quantitatively with local histologic ischemic changes in the setting of ischemic cardiac injury. In patients with cardiac scars and aneurysms from prior myocardial infarctions, voltage mapping with unipolar electrograms reliably differentiates normally perfused myocardium from fixed perfusion defects, and also identifies nonviable zones within the perfusion defects. In the study by Keck et al, the unipolar voltage findings correlated well with findings from Positron Emission Tomography (PET) glucose utilization. Bipolar electrograms are often difficult to interpret especially when the signals are fractionated (when they have multiple deflections). In contrast, the interpretation of the unipolar electrogram is straightforward, even under abnormal conditions and this feature is its great strength.

Figure 7:
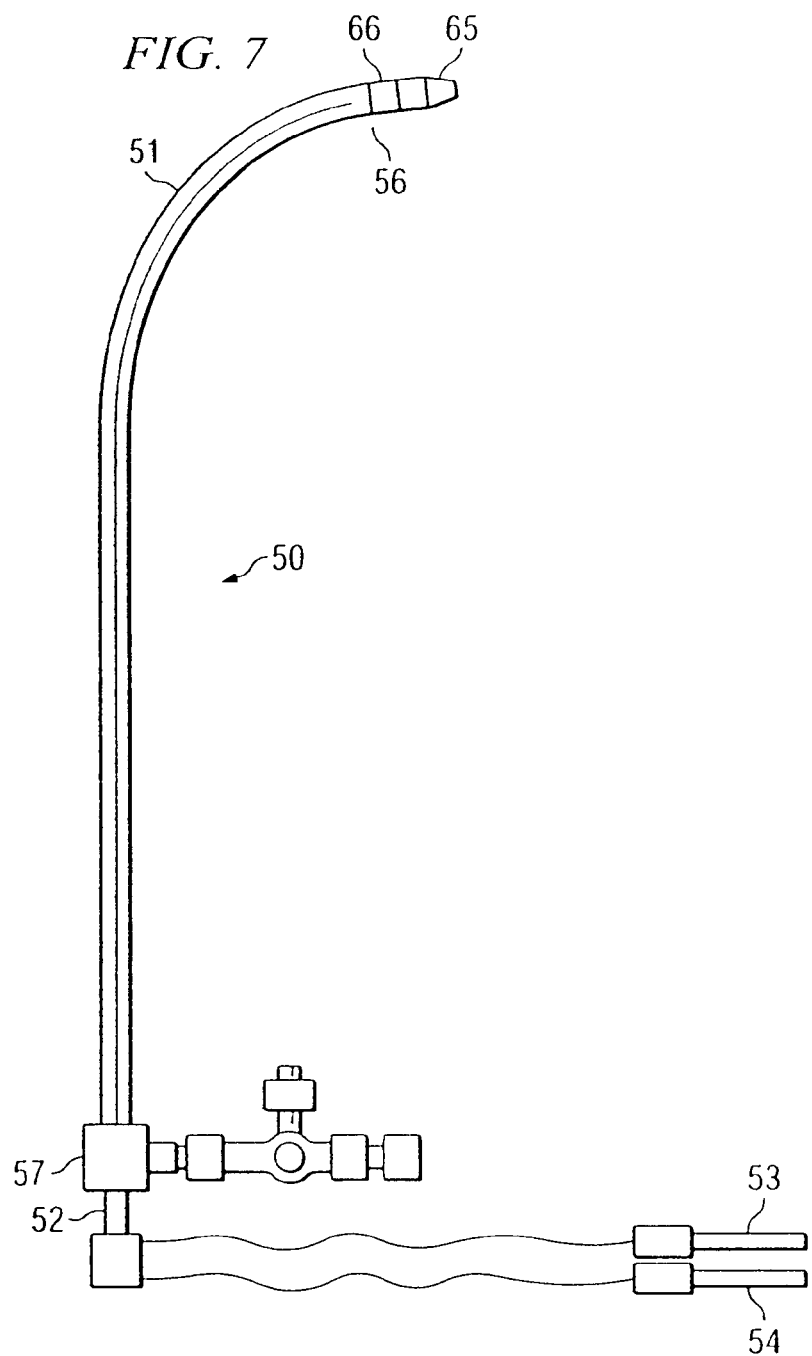
FIG. 7 is a schematic illustration of a transseptal apparatus according to one embodiment of the present invention.
Figure 8:
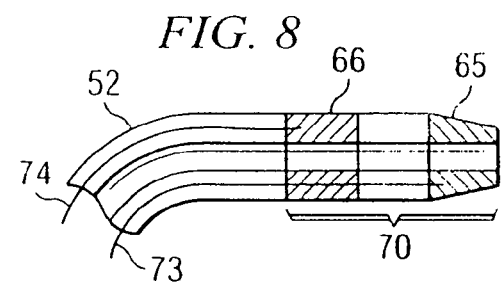
FIG. 8 is a cross-sectional view of the distal portion of the catheter of the transseptal apparatus shown in FIG. 7.

FIGS. 7 and 8 depict a transseptal apparatus 50 according to the present invention which may be used to not only locate the fossa ovalis but also to perform a transseptal puncture. Transseptal apparatus 50 is similar to conventional transseptal apparatus in that it includes a hollow sheath 51 and an internal catheter (sometimes referred to as a dilator) 52. Catheter 52 is hollow and is slightly longer than sheath 51 (typically about 4 cm longer). As is known to those skilled in the art, a guidewire is inserted through the right femoral vein and advanced to the superior vena cava. Catheter (or dilator) 52 is inserted into sheath 51, with the distal end of the catheter protruding beyond the distal end 56 of sheath 51. The sheath and catheter are then advanced over the guidewire into the superior vena cava. The guidewire is then removed.

Not only is the distal end 70 of catheter 52 tapered in the conventional manner, a pair of electrodes 65 and 66 are provided at the distal end of catheter 52. First, or distal, electrode 65 is provided at the tip of catheter 52, and second, or proximal, electrode 66 may also be provided at the distal end of catheter 52, spaced proximally from first electrode 65 by a distance of between about 2 and about 4 mm. The electrodes may, for example, be ring-shaped, with the first electrode measuring between about 2 mm and about 4 mm in length, and the second electrode measuring about 2 mm in length. Electrical leads 73 and 74 are in electrical communication with first and second electrodes 65 and 66, respectively. At the proximal end of catheter 52, electrical leads 73 and 74 are in electrical communication with cables 53 and 54, respectively, which may be attached to a differential amplifier or other device for generating electrograms. In this manner, the tip portion 70 of catheter 52 will function as an electrophysiology mapping catheter (both bipolar and unipolar), and will also serve the same function as a catheter/dilator in a conventional transseptal apparatus.

FIGS. 9-11 depict the use of transseptal apparatus 70 in a transseptal puncture using unipolar electrograms to locate the fossa ovalis. Since only unipolar measurements are depicted, the second electrode has been omitted from the tip 70 of catheter 52. However, it should be noted that, even if second electrode 66 is provided on catheter 52, the catheter can still be used for unipolar (as well as bipolar) measurements. In FIG. 9, transseptal apparatus 50 has been inserted into the patient's femoral vein until the distal tip 70 of the catheter/dilator is located within superior vena cava. The electrical lead from electrode 65 on tip 70 is used as the positive input to a differential amplifier, while a skin patch 75 serves as the reference electrode and is attached to the negative input to the differential amplifier via a wire or other lead. Distal tip 70 having first electrode 65 is then dragged inferiorly along the interatrial septum while the operator monitors the electrophysiological parameters for indication that the distal tip 70 has made contact with the fossa ovalis. One or more of the indicators described previously may be employed to make this determination. In addition, the operator may also observe ST segment elevation in order to confirm that the distal tip 70 is exerting significant pressure against the fossa ovalis.

Once the operator has confirmed the location of the fossa ovalis and that the distal tip 70 is in good contact with the fossa ovalis, a needle may be urged through the central lumen of catheter 52 until the tip of the needle protrudes beyond distal tip 70 through the fossa ovalis and into the left atrium. Thereafter, the catheter 52 may be urged through the fossa ovalis, followed by sheath 51. The catheter 52 and needle are then removed from sheath 51, leaving sheath 51 extending through the fossa ovalis into the left atrium.

FIG. 10 depicts an alternative arrangement wherein the Wilson's central terminal is used as the reference electrode. Wilson's central terminal is created by connecting all three limb electrodes through a 5000 ohm resistor. This terminal is used as the negative pole.

FIG. 11 depicts yet another alternative arrangement wherein an indifferent electrode 76 is positioned in the inferior vena cava. A separate catheter that is connected to the negative input of the amplifier may also be placed in one of the great veins.

I claim:

1. A method of identifying the fossa ovalis in a patient, the method comprising:
 (a) providing an electrophysiology catheter including at least a pair of electrodes coupled to a portion of the catheter;
 (b) advancing a guidewire through a lumen within the catheter and into a patient's heart;
 (c) deploying the catheter over the guidewire so as to position the electrodes against the surface tissue of the interatrial septum of the patient;
 (d) acquiring one of a plurality of a unipolar electrogram and a bipolar electrogram of the surface tissue of the interatrial septum while moving the electrodes to a plurality of positions against the surface tissue of the interatrial septum; and (e) identifying the fossa ovalis on the basis of at least one of the following parameters: a unipolar voltage reduction, a signal fractionation, a broadened signal, a reduced signal slew rate, a reduced local myocardial impedance, an increased phase angle and an increased pacing threshold.

2. The method of claim 1, wherein the fossa ovalis is also identified on the basis of bipolar voltage reduction and further comprising producing a signal indicating that the fossa ovalis has been identified.

3. The method of claim 1, wherein the fossa ovalis is identified on the basis of at least two of the following parameters: a unipolar voltage reduction, a signal fractionation, a broadened signal, a reduced signal slew rate, a reduced local myocardial impedance, an increased phase angle and an increased pacing threshold.

4. The method of claim 1, wherein the fossa ovalis is identified on the basis of unipolar voltage reduction.

5. The method of claim 1, wherein the catheter is configured and dimensioned to receive a medical device therethrough such that a distal end of the medical device emerges from a distal end of the catheter.

6. The method of claim 5, wherein the catheter is a transseptal dilator and the medical device is a transseptal puncture needle.

7. A method of performing a transseptal puncture on a patient, the method comprising:

(a) providing an electrophysiology catheter including at least a pair of electrodes and an open proximal end and an open distal end configured to pass a guidewire therethrough;

(b) advancing the catheter into a patient's heart over the guidewire;

(c) positioning the electrodes against the surface tissue of the interatrial septum of the patient;

(d) acquiring one of a unipolar electrogram and a bipolar electrogram of the surface tissue of the interatrial septum, while moving the electrodes to a plurality of positions against the surface tissue of the interatrial septum;

(e) identifying the fossa ovalis on the basis of at least one of the following parameters: a unipolar voltage reduction, a signal fractionation, a broadened signal, a reduced signal slew rate, a reduced local myocardial impedance, an increased phase angle and an increased pacing threshold; and (f) penetrating the surface tissue of the interatrial septum through the fossa ovalis in order to access the left atrium.

8. The method of claim 7, wherein the are disposed in spaced-apart relation on a portion of the distal end of the catheter and the positioning step comprises positioning the distal end of the catheter against the tissue of the interatrial septum of the patient.

9. The method of claim 8, wherein two electrodes are provided on the catheter, one of the electrodes at the distal end of the catheter and the other of the electrodes located on the catheter proximal to the other electrode.

10. The method of claim 8, wherein the bipolar electrogram and the unipolar electrogram are acquired and the method further comprising observing ST segment elevation in the unipolar electrogram in order to ensure that the distal end of the catheter is in contact with the tissue of the interatrial septum.

11. The method of claim 7, wherein the step of penetrating the interatrial septum comprises urging a needle portion through the interior of the catheter and through the fossa ovalis into the left atrium, wherein the needle portion comprises a distal portion of the guidewire.

12. The method of claim 11, further comprising the steps of:

inserting the guidewire through a femoral vein of the patient and advancing the guidewire to the superior vena cava;

inserting the catheter into a sheath;

advancing the sheath and the catheter over said guidewire into the superior vena cava in order to position the distal end of the catheter against the interatrial septum;

penetrating the interatrial septum with at least the needle portion;

after penetrating the interatrial septum, urging the catheter and the sheath through the fossa ovalis into the left atrium; and after the sheath has been urged through the fossa ovalis, removing the catheter and the needle portion from the sheath.

13. The method of claim 7, wherein the fossa ovalis is also identified on the basis of bipolar voltage reduction.

14. The method of claim 7, wherein the fossa ovalis is identified on the basis at least two of the following parameters: a unipolar voltage reduction, a signal fractionation, a broadened signal, a reduced signal slew rate, a reduced local myocardial impedance, an increased phase angle and an increased pacing threshold.

15. The method of claim 7, wherein the fossa ovalis is identified on the basis of unipolar voltage reduction.

16. The method of claim 7, further comprising positioning at least one indifferent electrode one of within and against the patient such that the at least one indifferent electrode may be used in conjunction with one of the one or more electrodes positioned against the interatrial septum in order to acquire unipolar electrograms.

17. The method of claim 16, wherein the at least one indifferent electrode is chosen from the group consisting of: a skin patch, a Wilson's central terminal, and an electrode positioned in a vein of the patent.

18. The method of claim 7, wherein the catheter is configured and dimensioned to receive a medical device therethrough such that a distal end of the medical device emerges from a distal end of the catheter.

19. The method of claim 18, wherein the catheter is a transseptal dilator and the medical device is a transseptal puncture needle.

* * * * *